United States Patent [19]

Van Horn et al.

[11] Patent Number: 5,136,087
[45] Date of Patent: Aug. 4, 1992

[54] PREPARATION OF POLYMETHYLENE POLYPHENYL POLYISOCYANATE

[75] Inventors: Irvin Van Horn, Webster; Ralph W. Hodges, Jr., Houston; Susan M. Strausser, Baytown, all of Tex.

[73] Assignee: Miles Inc., Pittsburgh, Pa.

[21] Appl. No.: 700,662

[22] Filed: May 15, 1991

[51] Int. Cl.$^5$ ............................................. C07C 263/10
[52] U.S. Cl. ................................... 560/352; 560/338; 560/347
[58] Field of Search .................... 560/338, 347, 352

[56] References Cited

U.S. PATENT DOCUMENTS

| | | | |
|---|---|---|---|
| 4,193,932 | 3/1980 | Yamamoto et al. | 560/352 X |
| 4,372,891 | 2/1983 | Hilbert et al. | 560/352 |
| 4,465,639 | 8/1984 | Hatfield, Jr. | 560/352 |
| 4,792,624 | 12/1988 | Hatfield, Jr. et al. | 564/333 |
| 4,876,380 | 10/1989 | Chen et al. | 560/352 |

*Primary Examiner*—Jose G. Dees
*Assistant Examiner*—Vera C. Clarke
*Attorney, Agent, or Firm*—Joseph C. Gil; Godfried R. Akorli

[57] ABSTRACT

Disclosed herein is an improved process for the preparation of polymethylene polyphenyl polyisocyanate by reacting phosgene with a corresponding polyamine, followed by removing residual phosgene from the reaction mixture, the improvement comprising removing the residual phosgene by contacting the reaction mixture which is maintained at 150 degrees Centigrade or lower, with an inert solvent vapor stream at a temperature which is sufficient to effect a substantially complete removal of the residual phosgene.

8 Claims, 1 Drawing Sheet

PREPARATION OF POLYMETHYLENE POLYPHENYL POLYISOCYANATE

BACKGROUND OF THE INVENTION

1. Field of the Invention

The present invention relates to the process for preparing polymethylene polyphenyl polyisocyanate by reacting phosgene with polyamines which correspond with the polyisocyanates. More specifically, present invention relates to the process for preparing lighter color polymeric polyisocyanates which are particularly useful in making lighter color foams.

2. Brief Description of the Prior Art

Discoloration of foams made with polymethylene polyphenyl polyisocyanates has, at least, in part been attributed to impurities in the polyisocyanates. Hence, attempts at solving the color problem has entailed treating the polyisocyanates or their precursors so as to remove the impurities therefrom or reduce their adverse effects on color.

U.S. Pat. No. 4,792,624 discloses that polymethylene polyphenyl polyisocyanates of improved color can be obtained from certain polyamines which are prepared by the following process. The process comprises the preparation of the corresponding polymethylene polyphenyl polyamine by condensing aniline and formaldehyde in the presence of an acid catalyst which is characterized by adding a minor proportion of a polyamine mixture comprising di(aminophenyl)methanes and oligomeric polymethylene polyphenyl polyamines, (collectively known as polymeric MDA to an intermediate stage of the condensation reaction where the various intermediately formed aminobenzylamines are present.

U.S. Pat. No. 4,465,639 discloses addition of controlled amounts of water to the reaction mixture produced by phosgenation of a mixture of polymethylene polyphenyl polyamines (and the like polyamines produced by condensation of formaldehyde and aromatic amines) prior to complete removal of excess phosgene gives rise to the corresponding polymethylene polyphenyl polyisocyanates having significantly improved properties such color of the polyisocyanates.

By the present invention, there is provided an alternate means of obtaining lighter color polyisocyanates.

SUMMARY OF THE INVENTION

In accordance with the foregoing, the claimed invention encompasses an improved process for the preparation of polymethylene polyphenyl polyisocyanate by reacting a phosgene with a corresponding polyamine, followed by removing residual phosgene from the reaction mixture, the improvement comprising removing the residual phosgene by contacting the reaction mixture which is maintained at 150 degrees Centigrade or lower, with an inert solvent vapor stream at a temperature which is sufficient to effect a substantially complete removal of the residual phosgene.

The process of the invention is advantaged by rapid dephosgenation, reduction in operating temperatures and gentler heating techniques; all of these lead to the reduction in color of the polyisocyanates which is manifested in the color of foams that are produced therewith. About fifty percent reduction in color can be obtained by the use of the process of this invention.

DETAILED DESCRIPTION OF THE INVENTION

Figure 1:
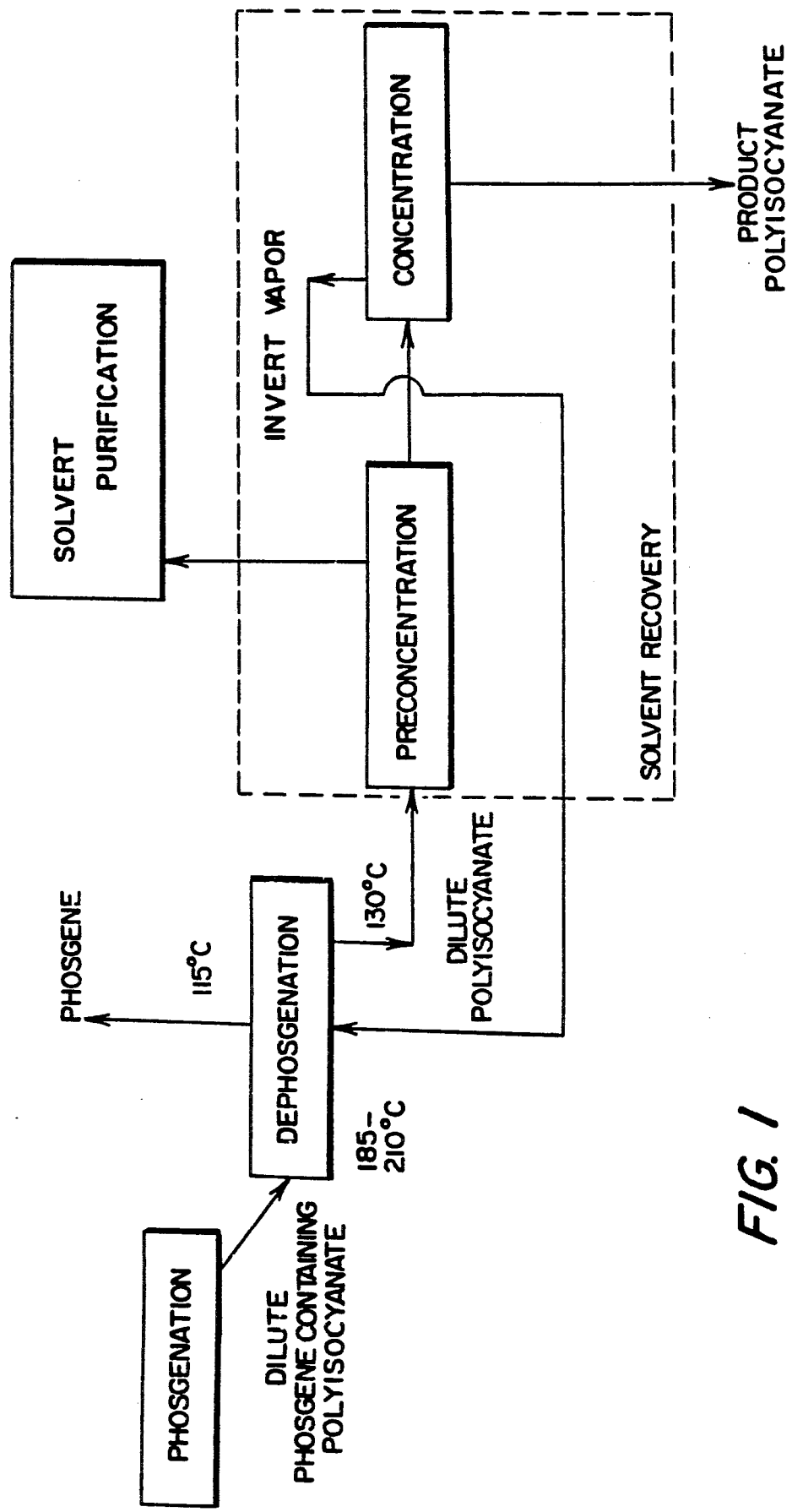
FIG. 1 is a line representation of the part of the reactor system suitable for the preparation of a polyisocyanate with particular reference to phosgenation, the removal of the residual phosgene with a solvent vapor stream, solvent purification and recovery of the polyisocyanate.

The reaction of phosgene with a polyamine corresponding to the desired polyisocyanates, alternately referred to as amine phosgenation, is conducted in the presence of an inert solvent such as chlorobenzene. The polyamines are prepared by the reaction of aniline with aldehydes, particularly formaldehydes in the presence of an acid catalyst such as hydrochloric acid. The polyamines are reacted with phosgene in molar ratios of 1.5 to 20 moles and preferably about 2.2 to 4.0 moles of phosgene per amine group. Upon completion of the phosgenation, the excess phosgene and hydrogen chloride formed are separately or simultaneously removed. The phosgenation product which is present after the removal is in the form of a solution and may be separated (e.g., by simple evaporation) into a gaseous phase containing volatile compounds having isocyanate groups and a liquid phase which is substantially completely crude polyisocyanate. The liquid phase can be worked up to produce polyisocyanates in a purer state.

In accordance with this invention, excess phosgene is removed from a liquid reaction mixture in a dephosgenation vessel, by contacting the reaction mixture containing the residual phosgene with a high temperature inert solvent vapor. All or virtually all of the phosgene is removed from the reaction mixture which is maintained at 150 degrees Centigrade or lower. Typically, the inert solvent vapor is at a temperature of about 170 to 220 degrees Centigrade and preferably from 185 to 210 degrees Centigrade, and pressure which can be up to 600 millimeters (mm) of mercury (Hg) and preferably from 450 to 550 (mm Hg).

The inert solvents that are useful in generating the high temperature inert solvent vapor can be some of the commonly used solvents in phosgenation processes. Illustrative but non-limiting examples of the inert solvent can be chlorobenzene, o-dichlorobenzene, mixed dichlorobenzenes, chlorotoluene and a mixture thereof. The inert solvent vapor can be introduced into the distillation column at a rate that is effective to remove the residual phosgene. Typically the inert solvent vapor is introduced at a weight rate of one-half to one times the weight rate of the reaction mixture and preferably from about 0.6 to 0.7 times the weight rate of the reaction mixture.

The vapor phase of the inert solvent can be conveniently obtained from a later stage in the process, for example, from the solvent recovery section of the process. Illustratively, the vapor phase of inert solvent is obtained by flash heating dilute crude polyisocyanate to a temperature of about 185 to 210 degrees Centigrade to evaporate inert solvent therefrom. The resulting solvent vapor phase is then introduced by appropriate pipings into the dephosgenation column. In accordance with the invention, the inert solvent vapor can contain from about 1-6 percent high boiling recyclable components. By the term "high boiling recyclable components" is meant that said components boil at a temperature which is higher that the rest of the solvent. Non-limiting examples of the high boiling components can be isocyanate impurities such as diphenylmethane diisocyanate or other polyisocyanates, inert solvents such as o-dichlorobenzene, or p-dichlorobenzene or the like.

In the practice of the invention, the reaction mixture is introduced into a dephosgenation vessel wherein it is contacted with the inert solvent vapor. The dephosgenation vessel typically comprises a distillation column. Preferably, the reaction mixture is contacted with the inert solvent vapor immediately upon the completion of the preparation of the product polyisocyanate. The contact time can be from about 2.5 to 6 minutes and preferably from about 2.5 to 3 minutes. It is a distinct feature of the invention that with minimal heat stress, the vapor phase of the inert solvent, by direct contact, effects the removal of phosgene. The inlet stream of the reaction mixture in the dephosgenation column is heated without changing the solvent dilution of the reaction mixture.

It is also a distinct feature of the invention that the dephosgenation column removes high boiling components such as isocyanate impurities from the rest of the solvent. Thus one obtains a solvent of improved purity for use in other parts of the process. The high boiling components are removed by heat and mass transfer with the reaction mixture causing condensation of the high boiling components and simultaneous vaporization of the phosgene in the reaction mixture.

The resulting reaction mixture is recovered by art-known techniques to obtain the product polyisocyanates. Foams that are prepared with the polyisocyanates which are obtained by the process of the invention exhibit a marked improvement in color, therewith.

In the practice of the invention, the process can be employed in preparing a variety of polyisocyanates.

The invention is further described by the following non-limiting examples.

EXAMPLES

In a properly equipped phosgenation reactor, the phosgenation of polymethylene polyphenyl polyamine containing about 45% methylene dianiline was carried out in chlorobenzene with a 110% molar excess of phosgene. The total solvent to amine weight ratio in the reaction mixture was about 12.5. The reaction of the phosgene and polyamine was completed by heating the reaction mixture to 92 degrees Centigrade.

The resulting solution of the product polyisocyanate and phosgene was introduced into the top of a a typical trayed dephosgenation column. A chlorobenzene vapor stream containing 4.7% polyisocyanates, at 204 degrees Centigrade, was introduced into the bottom of the dephosgenation column, at the rate of 0.6 times the weight rate of the reaction mixture. The column pressure was maintained 545 mm Hg with a sump temperature of 129 degrees Centigrade, for a period of 2.5 minutes.

The overhead vapor stream of the column which was free of polyisocyanates was recycled to the polyamine reaction section. The bottom stream was processed in two steps to remove all the chlorobenzene which was returned to the process. The first step comprised a fractional distillation where essentially pure chlorobenzene was recovered for use in the reaction of polyamines. The second step comprised a flash concentration to remove residual chlorobenzene and also requires flashing of some of the product polyisocyanate. The resulting vapor stream is returned to the dephosgenation process. The product polyisocyanate was recovered by additional distillation and flash separation techniques.

A comparison was made of a chlorobenzene-free polyisocyanate of the above process with that of a process where there was no separate dephosgenation step and where the residual phosgene was allowed to pass into the solvent recovery section, at temperatures of 165–200 degrees Centigrade. The product using the dephosgenation column had a 53% reduction in color intensity as measured by ultra violet (UV) visible spectrophotometer at 430 nm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In an improved process for the preparation of polymethylene polyphenyl polyisocyanate by reacting phosgene with a corresponding polyamine, followed by removing residual phosgene from the reaction mixture, the improvement comprising removing the residual phosgene by contacting the reaction mixture which is maintained at 150 degrees Centigrade or lower, with an inert solvent vapor stream at a temperature which is sufficient to effect a substantially complete removal of the residual phosgene; said inert solvent is selected from the group consisting of chlorobenzene, o-dichlorobenzene, mixed chlorobenzene, chlorotoluene and mixtures thereof.

2. The process of claim 1 wherein the insert solvent vapor is at a temperature of about 170 to 220 degrees Centigrade.

3. The process of claim 2 wherein the inert solvent vapor is at a temperature of about 185 to 210 degrees Centigrade.

4. The process of claim 1 wherein the residual phosgene is contacted with the inert solvent vapor stream in a distillation column.

5. The process of claim 1 wherein the inert solvent is chlorobenzene.

6. The process of claim 1 which further includes a solvent recovery section.

7. The process of claim 1 wherein the insert solvent contains a high boiling component.

8. The process of claim 7 further comprising removing the high boiling component from the insert solvent.

* * * * *